(12) United States Patent
Lundqvist

(10) Patent No.: US 7,022,136 B2
(45) Date of Patent: Apr. 4, 2006

(54) STENT FOR NEUTRON CAPTURE THERAPY AND METHOD OF MANUFACTURE THEREFOR

(75) Inventor: Hans Lundqvist, Uppsala (SE)

(73) Assignee: Abbott Laboratories Vascular Entities Limited, Galway (IE)

(*) Notice: Subject to any disclaimer, the term of this patent is extended or adjusted under 35 U.S.C. 154(b) by 475 days.

(21) Appl. No.: 10/016,044

(22) Filed: Dec. 11, 2001

(65) Prior Publication Data

US 2002/0133220 A1    Sep. 19, 2002

(51) Int. Cl.
*A61F 2/06* (2006.01)

(52) U.S. Cl. .............. 623/1.42; 600/2; 600/3

(58) Field of Classification Search .............. 623/1.15, 623/1.42–1.46; 600/1–8
See application file for complete search history.

(56) References Cited

U.S. PATENT DOCUMENTS

| 5,286,853 | A | * | 2/1994 | Spielvogel et al. ........... 534/16 |
|---|---|---|---|---|
| 5,575,749 | A | * | 11/1996 | Liprie ........................... 600/3 |
| 5,728,042 | A | | 3/1998 | Schwager |
| 5,730,698 | A | | 3/1998 | Fischell et al. |
| 5,782,742 | A | | 7/1998 | Crocker et al. |
| 5,840,009 | A | | 11/1998 | Fischell et al. |
| 6,183,409 | B1 | * | 2/2001 | Armini ........................... 600/3 |
| 6,319,189 | B1 | * | 11/2001 | Halpern et al. ................. 600/3 |
| 6,638,924 | B1 | * | 10/2003 | Mody et al. ................. 514/185 |

FOREIGN PATENT DOCUMENTS

EP    0 857 470    8/1998

* cited by examiner

*Primary Examiner*—(Jackie) Tan-Uyen T. Ho
(74) *Attorney, Agent, or Firm*—Nicola A. Pisano, Esq.; Luce, Forward, Hamilton & Scripps LLP

(57) ABSTRACT

Improved method and apparatus for neutron capture therapy are provided that may beneficially be used to counteract restenosis wherein a stent comprises a stable nuclide having a large neutron capture cross-section that may be irradiated with thermal neutrons applied by an external source, after placement of the stent, thereby giving rise to therapeutic radiation in the proximity of the stent. Because the stent only contains stable nuclides, it can be handled without the precautions needed when handling radioactive matter. An improved stent and a method for manufacturing the stent also are provided.

26 Claims, 2 Drawing Sheets

STENT FOR NEUTRON CAPTURE THERAPY AND METHOD OF MANUFACTURE THEREFOR

FIELD OF THE INVENTION

The present invention relates to intravascular neutron capture therapy. More particularly, the present invention provides methods and apparatus for making and using an implantable stent comprising a material capable of reducing restenosis, thereby improving long-term patency of the implanted stent.

BACKGROUND OF THE INVENTION

Over the past 20 years, the number of percutaneous coronary revascularization procedures has increased to more than one million per year. About 50% of these procedures include stent implantation. A stent is often designed as a thin metal wire mesh, which keeps a fabric in a desired shape, for instance forming a very thin tube providing an open channel for a fluid. FIG. 1 illustrates an example of such a stent, which is commercially available from JOMED AB, Helsingborg, Sweden. A polyfluorotetraethylene ("PFTE") graft material integrated into the stent is used to seal off a perforated or ruptured artery wall.

One drawback associated with previously known stents is the restenosis effect, i.e., the epithelial cells of the vessel walls adjacent to the ends of the stent and surrounding the stent may experience excess growth of cells, thereby clogging the vessel.

One way to decrease the risk of restenosis is to irradiate the vessel in the vicinity of the stent. The cell proliferation rate is thereby decreased, and the vessel remains patent. Several ways to apply local radiation doses have been investigated, including temporarily placing balloons filled with radioactive solution inside the stent area or placing radioactive wires. Previously known radioactive stents used in clinical trials are activated by reactor or accelerator irradiation. Irradiation by small X-ray tubes inserted into the coronary arteries through a guide catheter has also been suggested, and there is still considerable discussion about the best radiation delivery system.

U.S. Pat. No. 5,728,042 to Schwager describes an appliance comprising a core wire on which is mounted a coil of radioactive material. A first proximal radiopaque coil configuration and a second distal radiopaque coil configuration maintain and locate the radioactive radiation coil on the core wire, thereby ensuring positioning thereof on the core and ensuring accurate visualization via X-ray fluoroscopy.

U.S. Pat. No. 5,782,742 to Crocker et al. discloses a balloon catheter with an inflatable balloon having thereon a radiation carrier such as a radiation delivery metal foil, such as gold. The foil is irradiated, and the balloon is thereafter positioned at a treatment site in a vessel and expanded to bring the metal foil layer into close proximity with the vessel wall. In another embodiment, the radiation carrier is in the form of a dopant in the balloon material. A PE or PET multi-layer or single layer balloon can be extruded with sodium phosphate (monobasic, dibasic or tribasic) as a filler. The phosphate filled balloon can be placed in a neutron beam to produce sodium phosphate P-32. Other suggested radiation delivery sources are Y-90, Au-198, Ir-192 and Mo-99.

German publication DE 197 54 870 Al to Alt discloses a stent with an expandable perforated tube. The tube has a cover containing a biocompatible carrier containing a radioactive material, which is P-32 or Au-198. The radioactive material has an activity level of about one micro-Curie.

U.S. Pat. No. 5,730,698 to Fischell et al. discloses an expandable temporary stent system, including an over-the-wire balloon angioplasty catheter. The balloon angioplasty catheter has a proximal section that remains outside the body. A stent assembly is slidably mounted on the balloon angioplasty catheter in a coaxial manner and has a proximal section and a distal section, where a temporary stent is located at the distal section. The system further comprises a radiation shield over the stent assembly. The patent also discloses a method for treatment of arterial stenosis by means of the stent system.

Several problems are common to all devices for this type of intravascular brachytherapy. Dimensions are small, and misplacement of the radiation source by as little as a few millimeters can give rise to a very inaccurate dose distribution. Normally, radiation is delivered in conjunction with balloon catheterization, before one knows whether or not radiation therapy is necessary. Furthermore, working with radioactive sources in a catheterization laboratory is problematic, as a new catheterization has to be performed, thereby adding risk to the patient and costs to the treatment.

In view of the foregoing, it would be desirable to provide apparatus and methods for neutron capture therapy that provide temporal separation during a stenting procedure between balloon dilatation following stenting and delivery of radiation.

It further would be desirable to provide methods and apparatus that ensure neutron capture therapy is only provided to patients where radiation exposure is expected to provide therapeutic benefit.

It still further would be desirable to provide methods and apparatus for neutron capture therapy that allow therapy to be repeated as needed.

SUMMARY OF THE INVENTION

In view of the foregoing, it is an object of the present invention to provide methods and apparatus for neutron capture therapy that provide temporal separation during a stenting procedure between balloon dilation following stenting and delivery of radiation.

It is another object to provide methods and apparatus that ensure neutron capture therapy is only provided to patients where radiation exposure is expected to provide therapeutic benefit.

It is yet another object to provide methods and apparatus for neutron capture therapy that allow therapy to be repeated as needed.

These and other objects are accomplished by providing a stent having a stable target nuclide with a large capture cross-section for thermal neutrons. This nuclide is preferably incorporated as an alloy in the stent. When there is a clinical need for neutron capture therapy, the stent is irradiated with thermal neutrons, thereby giving rise to ionization radiation around the stent device. Concentration of target nuclide and thermal neutron flux determines dose rate around the stent. Since radiation is applied by an external source, it can be delivered at any time after placement of the stent and easily may be repeated.

Methods for making the stent according to the present invention are also provided.

BRIEF DESCRIPTION OF THE DRAWINGS

The above and other objects and advantages of the present invention will be apparent upon consideration of the following detailed description, taken in conjunction with the accompanying drawings, in which.

DETAILED DESCRIPTION OF THE INVENTION

The present invention provides a stent comprising a stable nuclide element that may be externally activated by thermal neutrons, thereby providing localized neutron capture therapy in the vicinity of the vessel around the stent. Since radiation is applied by an external source, therapy may be delivered at any time after placement of the stent and easily may be repeated. Furthermore, unlike other known radiation techniques, the present invention ensures that neutron capture therapy is only provided to patients where radiation exposure is expected to provide therapeutic benefit.

In accordance with the principles of the present invention, a stent is constructed including a material having a high neutron capture cross-section, for example, greater than $10^3$ barns, and that provides a high quality of radiation emission. As will of course be apparent, the irradiation dose provided by the stent after irradiation by an external source also depends upon the amount of stable nuclide element that is incorporated into the stent. Preferred stable nuclides suitable for use in a stent constructed in accordance with the present invention are listed below with their corresponding thermal neutron capture cross-sections.

| Atomic element | Cross-section (barn) |
| --- | --- |
| $^{157}$Gd | 254000 |
| $^{155}$Gd | 60900 |
| $^{149}$Sm | 40140 |
| $^{113}$Cd | 20600 |
| $^{151}$Eu | 5900 |

Bulk materials with which these nuclide elements may be combined to form a stent or other interventional device for neutron capture therapy are provided below, again with corresponding thermal neutron capture cross-sections. Preferably, the bulk materials have significantly lower neutron cross-sections compared to the elements employed for neutron capture, generally less than $10^2$ barns.

| Atomic element | Cross-section (barn) |
| --- | --- |
| $^{198}$Au | 98 |
| $^{59}$Co | 20 |
| $^{48}$Ti | 7.8 |
| $^{109}$Ag | 4.5 |
| $^{107}$Ag | 3.0 |
| $^{56}$Fe | 2.6 |

While these bulk materials may produce a small amount of ionization radiation when subjected to thermal neutron radiation, the contribution of this ionization radiation to a composite absorbed dose is negligible.

In a preferred embodiment, a stent for neutron capture therapy comprises gadolinium as the stable nuclide. Gadolinium is a trivalent metallic element and is a member of the rare earth group. Its atomic number is 64, and it has a relative atomic mass of 157.25. Gadolinium has the largest known thermal neutron capture cross-section (254000 barn) of any element. The most frequent stable Gadolinium nuclide is denoted as Gd-157. Gd-157 makes up 15.65% of all Gadolinium, and it primarily radiates energy in the form of high-energy gamma radiation.

Figure 1:
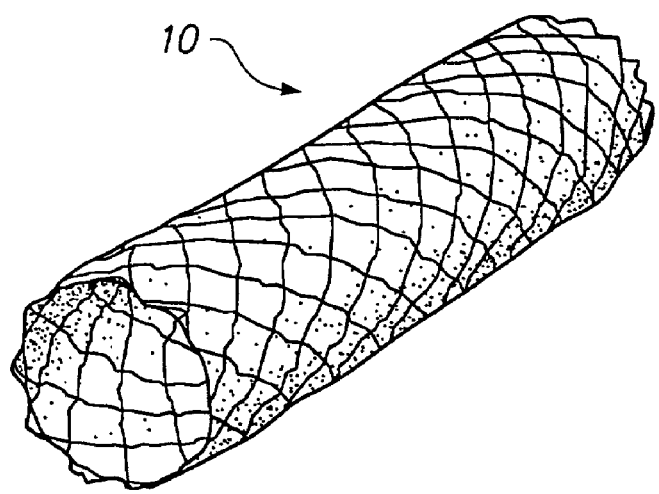
FIG. 1 is an isometric view of a prior art stent.

A previously known stent, for example, such as depicted in FIG. 1, typically may weigh on the order of 40 mg. The amount of stable nuclide incorporated into such a stent in accordance with the principles of the present invention may be chosen based upon a variety of design considerations. For the purposes of illustration, assume an enriched target of N atoms of Gd-157 and a neutron flux of n thermal neutrons/cm2/s. The number of neutron captures per second, Ac, may be computed as: $Ac = n \cdot N \cdot 2.54 \cdot 10^{-9}$. 1 mg of Gd-157 ($N = 3.8 \cdot 10^{18}$ atoms), which radiates neutrons at a rate of approximately $n = 10^8$ neutrons/$cm^2$/s, provides an Ac of about $9.7 \cdot 10^7$ captures per second. This is equivalent to a radioactive source with a strength of $9.7 \cdot 10^7$ Bq.

Figure 2:
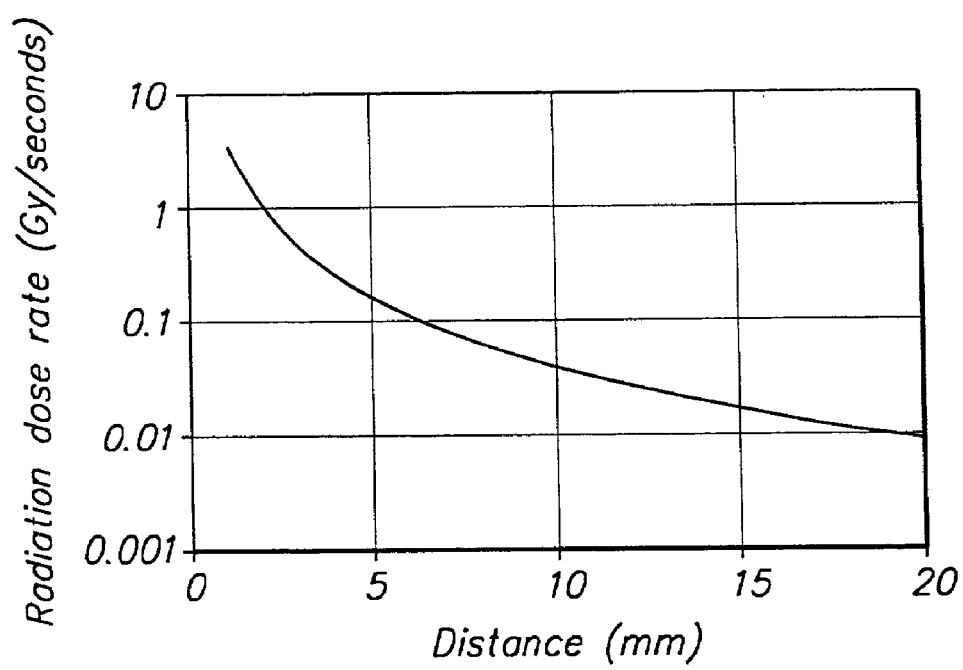
FIG. 2 is a graph illustrating calculation of the KERMA dose rate around a point source created by irradiation of 1 mg Gd-157 with $10^8$ thermal neutrons per second per $cm^2$.
Figure 3:
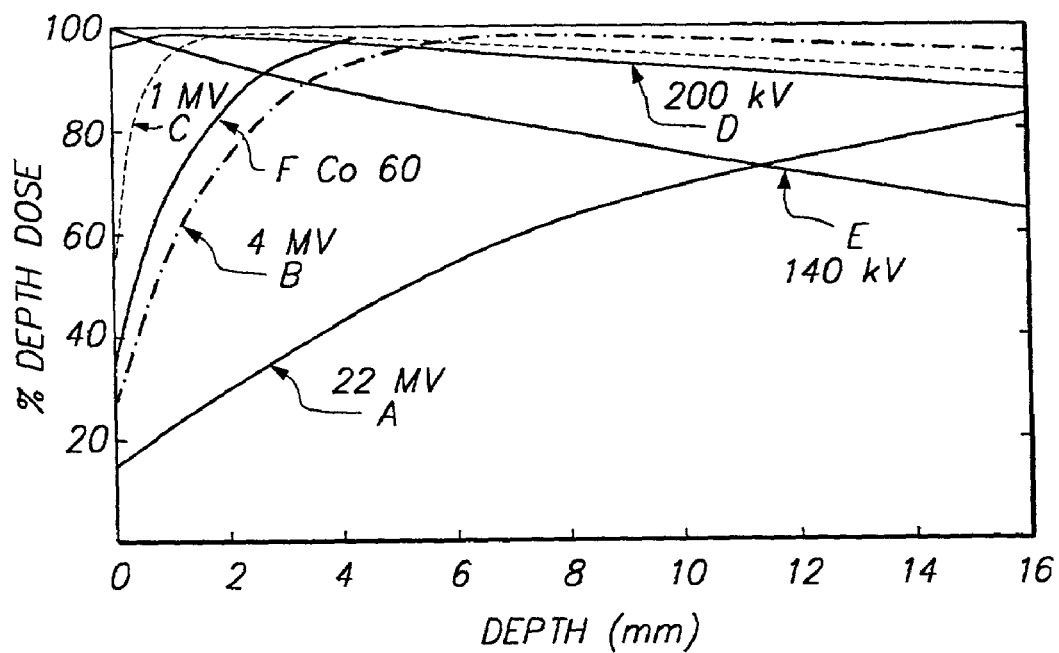
FIG. 3 is a graph illustrating build-up zones from different qualities of gamma and X-ray radiation.

From the gamma spectrum of Gd-157, the Γ-constant may be determined as 1.28 Gy/h/$m^2$, and the dose rate distribution may be determined for a point source containing the 1 mg of Gd-157. FIG. 2 presents this dose rate distribution in a thermal neutron field of $10^8$ n/$cm^2$/s. The dose obtained from this calculation reflects a KERMA value rather than an actual absorbed dose. Gamma energies emitted are fairly high, on the order of several MeV. These energies may have build-up zones of several millimeters, as seen in FIG. 3. The build-up zones level out the dose close to the source and compensate for the square-law dependence at the closest distances from the stent. This is an advantage of the present invention when compared to other radiation techniques that use high-energy beta or low-energy gamma sources having negligible build-up zones.

According to these illustrative calculations, a therapeutic radiation dose may be delivered within a few seconds (<10 seconds in a distributed source). The dose contribution of the neutrons themselves, distributed as a general background, yield a dose far below biologically dangerous levels.

In this example, the dose rate is expected to be about 1 Gy/second in the area closest to the source, as seen in FIG. 2. The required dose may then be delivered in 10–30 seconds, or somewhat longer (in a couple of minutes) if the source is extended to offer a larger area, such as stent 20 of FIG. 4. Stent 20 is fabricated from a material incorporating stable nuclide element S. This example indicates that therapeutic dose rates may be delivered within clinically acceptable parameters. Corresponding calculations according to the above example also may be performed for the other listed atomic elements. It will be apparent to those of skill in the art that the amount of stable element S may be tailored to specific patient populations.

Figure 4:
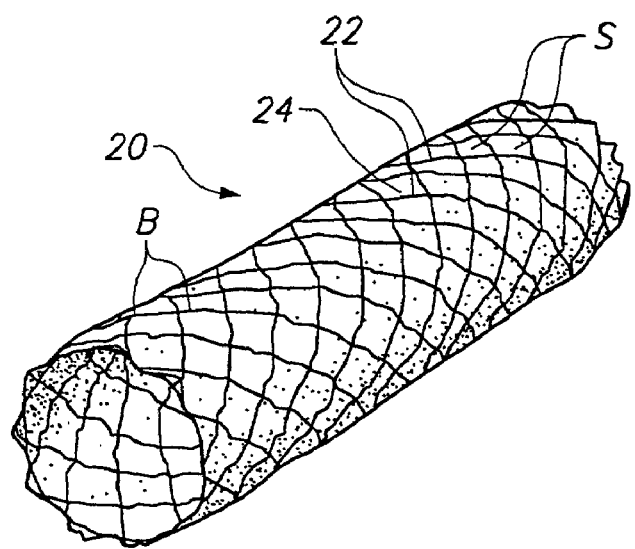
FIG. 4 is an isometric view of a stent in accordance with the present invention.

Referring still to FIG. 4, stent 20 may comprise metal wire mesh 22 that is fabricated from an alloy or mix incorporating from a few tens to a few hundreds of micrograms of the desired stable nuclide S. In another embodiment, wire mesh 22 may comprise hollow wires in which stable element S is located. Wire mesh 22 is preferably coated with a biocompatible material B to prevent direct contact between body tissue and the wire mesh metal containing stable nuclide S. Also, stent 20 optionally may include fabric 24, thereby providing a continuous tubular profile to stent 20.

The % composition, as well as the nuclide or nuclides comprising stable element S, may be varied within stent 20 to obtain a differentiation of radiation along stent 20. In some applications, creating a larger radiation dose at the ends of the stent, where restenosis may be more pronounced, is expected to be advantageous.

A method of using stent 20 is now described. Stent 20 is deployed at a treatment site within a patient's vasculature using well known percutaneous or subcutaneous techniques. When neutron capture therapy is deemed therapeutically beneficial, the patient is subjected to external radiation near the treatment site at clinically-acceptable levels that minimize damage to biological tissue. Due to its high neutron capture cross-section, stable nuclide element S preferentially absorbs and emits the radiation to tissue at the treatment site surrounding stent 20, thereby providing localized radiation therapy in a concentrated dose. The emitted radiation acts on surrounding tissue to provide a therapeutic benefit, for example, to reduce the restenosis often encountered after angioplasty and stenting. The short half life of stable element S provides negligible radiation when not irradiated, as imposed activity decays in milliseconds after completion of thermal neutron irradiation.

An advantage of the stents constructed in accordance with the present invention is that the stents may be handled without concern for radiation exposure, as they contain only stable nuclides. A still further advantage is that when using, for example, Gd-157 as the neutron capture therapy element, a stent will only produce gamma radiation when subjected to neutron irradiation, as the lifetime of the active gadolinium is very short and decays in microseconds. As already noted, the primary wire mesh metal constituent of the stent will have a very small capture cross-section for neutron irradiation, but will not produce any harmful residual activity.

Irradiation using the present neutron capture therapy may advantageously be limited to when restenosis is observed, and the therapy may be applied repetitively, as needed. This avoids more extensive methods involving rearrangement of existing implanted stents or introduction of new stent devices, due to restenosis. It should be noted that, although stent 20 of FIG. 4 illustrates a device for use in connection with coronary dilatation, a general stent device according to the present invention may also be used in connection with any subcutaneous (or percutaneous) therapy, e.g., in connection with treatment of a tumor.

Radiation sources suitable for use with the stents of the present invention are known. For example, radiation sources capable of delivering a suitable number of thermal neutrons have been developed for boron neutron capture therapy (BNCT) and are expected to be readily applicable to neutron capture therapy in accordance with the present invention. Other sources, such as accelerators and radioactive sources delivering neutrons, may also be used with embodiments of the present invention.

Although preferred illustrative embodiments of the present invention are described above, it will be evident to one skilled in the art that various changes and modifications may be made without departing from the invention. For example, a wide variety of stent designs are known in the art; incorporation of stable nuclides into these designs for the purpose of neutron capture therapy falls within the present invention. It is intended in the appended claims to cover all such changes and modifications that fall within the true spirit and scope of the invention.

What is claimed is:

1. A stent for neutron capture therapy configured for implantation within a patient's body, the stent comprising a body portion fabricated from a material that incorporates a stable atomic element having a neutron capture cross-section greater than $10^3$ barns, and emits therapeutic irradiation substantially only while being exposed to a thermal neutron irradiation after implantation in the patient's body.

2. The stent of claim 1, wherein the stable atomic element is chosen from the group consisting of $^{157}$Gd, $^{155}$Gd, $^{149}$Sm, $^{113}$Cd and $^{151}$Eu.

3. The stent of claim 2, wherein the body portion comprises a metallic wire mesh.

4. The stent of claim 3, wherein the metallic wire mesh is fabricated from hollow wires, the stable atomic element located within the hollow wires.

5. The stent of claim 1, wherein the material comprises an alloy or mix incorporating the stable atomic element and a bulk material having a neutron capture cross-section less than $10^2$ barns.

6. The stent of claim 3, wherein the metallic wire mesh is fabricated from an alloy or mix incorporating the stable atomic element.

7. The stent of claim 1, wherein the body portion is coated with a biologically compatible material that prevents contact between body tissue and the stable atomic element.

8. The stent of claim 1, wherein the stable atomic element is incorporated into the stent in a nonuniform density to vary a radiation dose obtained during neutron radiation therapy.

9. The stent of claim 1, wherein the stable atomic element further comprises multiple stable atomic elements.

10. The stent of claim 3 further comprising a fabric in communication with the metallic wire mesh.

11. The stent of claim 10, wherein the fabric provides a continuous tubular profile to the stent.

12. The stent of claim 1 further comprising a radiation source in communication with the stable atomic element.

13. The stent of claim 12, wherein the radiation source comprises a radiation source suitable for boron neutron capture therapy.

14. The stent of claim 12, wherein the radiation source comprises an accelerator.

15. A method of manufacturing a stent for neutron capture therapy following implantation within a patient's body, the method comprising introducing a material into a body portion of the stent, the material incorporating a stable atomic element having a neutron capture cross-section suitable for radiation when subjected to neutron irradiation and that emits therapeutic radiation substantially only while being exposed to a thermal neutron irradiation after implantation in the patient's body.

16. The method of claim 15, wherein the radiation comprises localized temporal gamma radiation.

17. The method of claim 15, wherein introducing the material comprises introducing a stable atomic element chosen from the group consisting of $^{157}$Gd, $^{155}$Gd, $^{149}$Sm, $^{113}$Cd and $^{151}$Eu.

18. The method of claim 15, wherein introducing the material comprises alloying or mixing the material with a bulk material used to fabricate the body portion of the stent.

19. The method of claim 15 further comprising distributing the stable atomic element when forming the stent body to obtain a stent suited for distributed radiation when subjected to neutron irradiation.

20. A method of performing neutron capture therapy, the method comprising:

providing a stent comprising a body portion fabricated from a material that incorporates a stable atomic element, the element having a neutron capture cross-section greater than $10^3$ barns;

deploying the stent at a treatment site within a patient's vasculature; and externally irradiating the patient near the treatment site with a thermal neutron irradiation, the stable atomic element preferentially absorbing and emitting the radiation to tissue at the treatment site substantially only while being exposed to the thermal neutron irradiation.

21. The method of claim 20, wherein preferentially absorbing and emitting the radiation comprises providing localized radiation therapy to the treatment site in a concentrated dose.

22. The method of claim 20, wherein the emitted radiation acts on surrounding tissue to a therapeutic benefit.

23. The method of claim 22, wherein the therapeutic benefit comprises reducing restenosis encountered after an interventional procedure.

24. The method of claim 23, wherein the interventional procedure is chosen from the group consisting of angioplasty and stenting.

25. The method of claim 20, wherein providing a stent comprising a body portion fabricated from a material that incorporates a stable atomic element comprises providing a stable atomic element chosen from the group consisting of $^{157}Gd$, $^{155}Gd$, $^{149}Sm$, $^{113}Cd$ and $^{151}Eu$.

26. The method of claim 20, wherein the stable element has a half life on the order of milliseconds or less.

* * * * *